(12) United States Patent　　(10) Patent No.:　US 12,673,178 B2
Ishikita　　(45) Date of Patent:　Jul. 7, 2026

(54) VENTILATOR

(71) Applicant: Naoyuki Ishikita, Niigata (JP)

(72) Inventor: Naoyuki Ishikita, Niigata (JP)

( * ) Notice: Subject to any disclaimer, the term of this patent is extended or adjusted under 35 U.S.C. 154(b) by 705 days.

(21) Appl. No.: 18/005,428

(22) PCT Filed: Sep. 14, 2021

(86) PCT No.: PCT/JP2021/033702
§ 371 (c)(1),
(2) Date: Jan. 13, 2023

(87) PCT Pub. No.: WO2022/019342
PCT Pub. Date: Jan. 27, 2022

(65) Prior Publication Data
US 2023/0277799 A1　Sep. 7, 2023

(30) Foreign Application Priority Data
Jul. 18, 2020　(JP) ................................. 2020-123336

(51) Int. Cl.
A61M 16/20　　(2006.01)
A61M 16/01　　(2006.01)
(Continued)

(52) U.S. Cl.
CPC .......... A61M 16/209 (2014.02); A61M 16/01 (2013.01); A61M 16/0816 (2013.01);
(Continued)

(58) Field of Classification Search
CPC .............. A61M 16/00; A61M 16/0057; A61M 16/0816; A61M 16/0833; A61M 16/0883;
(Continued)

(56) References Cited

U.S. PATENT DOCUMENTS

| 2,588,157 | A | 3/1952 | Olson |
| 3,726,274 | A | 4/1973 | Bird et al. |
| | | (Continued) | |

FOREIGN PATENT DOCUMENTS

| CN | 2821327 | Y | 9/2006 |
| CN | 101761675 | A | 6/2010 |
| | | (Continued) | |

OTHER PUBLICATIONS

European Search Report for Patent Application No. EP21845191.2 (dated Jul. 2, 2024).

(Continued)

*Primary Examiner* — Joseph D. Boecker
(74) *Attorney, Agent, or Firm* — Future IP LLC; Tomoko Nakajima

(57) ABSTRACT

Provided is a new ventilator that can be used for pulmonary resuscitation without requiring an electrical driving source. A ventilator includes a housing. The housing has an input port through which a gas is introduced into the housing, a main port through which the gas that is to be sent to and inhaled by a patient and a gas that is exhaled by the patient pass, an exhaust port through which the gas inhaled or the gas exhaled is exhausted from the housing, a ventilation path connecting the input port and the main port to each other, and a relief valve that is opened by receiving a pressure from the ventilation path and that allows communication between the ventilation path and the exhaust port so as to release the pressure.

22 Claims, 11 Drawing Sheets

(51) Int. Cl.
*A61M 16/08* (2006.01)
*A61M 16/10* (2006.01)

(52) U.S. Cl.
CPC ...... *A61M 16/1045* (2013.01); *A61M 16/208* (2013.01); *A61M 2205/3344* (2013.01)

(58) Field of Classification Search
CPC .......... A61M 16/0891; A61M 16/1045; A61M 16/20; A61M 16/201; A61M 16/208; A61M 16/209; A61M 2205/3344; A61H 31/02
See application file for complete search history.

(56) References Cited

U.S. PATENT DOCUMENTS

| | | | | |
|---|---|---|---|---|
| 4,437,461 | A * | 3/1984 | Greenberg | A61M 16/20 |
| | | | | 415/125 |
| 4,932,434 | A | 6/1990 | Taylor | |
| 5,094,266 | A | 3/1992 | Ledbetter | |
| 5,203,372 | A | 4/1993 | Freiler | |
| 5,479,920 | A | 1/1996 | Piper et al. | |
| 5,632,298 | A * | 5/1997 | Artinian | A61M 16/205 |
| | | | | 128/204.19 |
| 5,988,162 | A | 11/1999 | Retallick, III | |
| 7,207,332 | B1 * | 4/2007 | Lugtigheid | A61M 16/0084 |
| | | | | 128/205.24 |
| 9,482,354 | B2 | 11/2016 | Girard et al. | |
| 9,964,217 | B2 | 5/2018 | Siebert | |
| 10,987,482 | B1 * | 4/2021 | Duis | A61M 16/0078 |
| 2005/0187500 | A1 | 8/2005 | Perry et al. | |
| 2005/0248045 | A1 | 11/2005 | Anthony | |
| 2006/0021661 | A1 | 2/2006 | Koch et al. | |
| 2006/0157116 | A1 | 7/2006 | Martin et al. | |
| 2007/0204922 | A1 * | 9/2007 | Owczarczak | F16K 31/084 |
| | | | | 137/601.19 |
| 2010/0199991 | A1 * | 8/2010 | Koledin | A61M 16/107 |
| | | | | 128/205.12 |
| 2011/0197892 | A1 * | 8/2011 | Koledin | A61M 16/0866 |
| | | | | 128/205.24 |
| 2012/0012111 | A1 | 1/2012 | Howe, Jr. et al. | |
| 2013/0118484 | A1 * | 5/2013 | Ishikita | A61M 16/01 |
| | | | | 128/200.14 |
| 2014/0053929 | A1 | 2/2014 | Zheng | |
| 2014/0283922 | A1 | 9/2014 | Strom et al. | |
| 2016/0097434 | A1 | 4/2016 | Russell et al. | |
| 2016/0256661 | A1 * | 9/2016 | Battersby | A61M 16/1045 |
| 2016/0346500 | A1 | 12/2016 | Howe, Jr. et al. | |
| 2019/0022346 | A1 * | 1/2019 | Ishikita | F16K 17/06 |
| 2020/0061319 | A1 * | 2/2020 | Hansmann | A61M 16/085 |

FOREIGN PATENT DOCUMENTS

| | | | |
|---|---|---|---|
| CN | 105102869 | A | 11/2015 |
| CN | 210301942 | U | 4/2020 |
| EA | 025719 | B1 | 5/2014 |
| EP | 0590289 | A1 | 4/1994 |
| EP | 1023099 | B1 | 4/2005 |
| GB | 949221 | A | 2/1964 |
| JP | 47-10873 | A | 4/1972 |
| JP | 51-128030 | U | 10/1976 |
| JP | 59-147964 | U | 10/1984 |
| JP | 1988285238 | A | 11/1988 |
| JP | 1-23878 | A | 9/1989 |
| JP | 2-113180 | A | 4/1990 |
| JP | H6-209997 | A | 8/1994 |
| JP | 1996010331 | A | 1/1996 |
| JP | 1997257136 | A | 9/1997 |
| JP | 2003-019201 | A | 1/2003 |
| JP | 2005527304 | A | 9/2005 |
| JP | 2005-288045 | A | 10/2005 |
| JP | 2010-522007 | A | 7/2010 |
| JP | 2011-182949 | A | 9/2011 |
| JP | 2013-017766 | A | 1/2013 |
| JP | 2013224701 | A | 10/2013 |
| JP | 2016075390 | A | 5/2016 |
| JP | 2016098974 | A | 5/2016 |
| JP | 2020115986 | A | 8/2020 |
| JP | D1674656 | S | 12/2020 |
| RU | 23048 | U1 | 5/2002 |
| RU | 2462277 | C1 | 9/2012 |
| RU | 2659136 | C2 | 11/2017 |
| RU | 2735638 | C1 | 11/2020 |
| WO | WO2012/165541 | A1 | 12/2012 |
| WO | 2015148752 | A1 | 10/2015 |
| WO | 2015191960 | A1 | 12/2015 |
| WO | WO2017/115866 | A1 | 7/2017 |

OTHER PUBLICATIONS

Chinese Office Action for Application No. 202180062474.7 (dated Jun. 14, 2025) and English translation thereof.
Russian Office Action for Application No. 2023111012/14(023537) (dated Dec. 20, 2024) and English translation thereof.
European Search Report for Patent Application No. EP21875209.5 (dated Sep. 16, 2024).
International Search Report and Written Opinion for PCT Patent App. No. PCT/JP2012/033702 (Nov. 2, 2021).
Japanese Notice of Reasons for Refusal for Patent Application No. 2020-123346 (dated May 21, 2024) with English language translation thereof.
Office Action for U.S. Appl. No. 18/246,897 (dated Feb. 26, 2026) (family patent).

* cited by examiner

VENTILATOR

This application is a national phase entry under 35 U.S.C. § 371 of PCT Patent Application No. PCT/JP2021/033702, filed Sep. 14, 2021, which claims priority under 35 U.S.C. § 119 to Japanese Patent Application No. 2020-123336, filed Jul. 18, 2020, which are incorporated by reference.

TECHNICAL FIELD

The present disclosure relates to a ventilator.

BACKGROUND ART

The inventor of the present invention has proposed a relief valve that has a simple structure in which a valve body is caused to perform opening and closing operations automatically and appropriately by the pressure of a gas (PTL 1). This relief valve does not require an electrical drive source and can be used as, for example, an adjustable pressure limiting (APL) valve included in a ventilator or an inhalation anesthesia apparatus.

CITATION LIST

Patent Literature

PTL 1: International Publication No. 2017/115866

SUMMARY OF INVENTION

Technical Problem

To the present inventor's knowledge, there is no device for a ventilator that has a simple structure, that does not require an electrical drive source, and that can be used as a ventilator like the above-mentioned relief valve. The present disclosure provides a new technology that can be used for pulmonary resuscitation.

Solution to Problem

An aspect of the present disclosure is a ventilator including a housing, and the housing has an input port through which a gas is introduced into the housing, a main port through which the gas that is to be sent to and inhaled by a patient and a gas that is exhaled by the patient pass, an exhaust port through which the gas inhaled or the gas exhaled is exhausted from the housing, a ventilation path connecting the input port and the main port to each other, and a relief valve that is opened by receiving a pressure from the ventilation path and that allows communication between the ventilation path and the exhaust port in such a manner as to release the pressure.

According to the aspect of the present disclosure, a ventilator (a relief valve that has a function of serving as a ventilator) having a simple structure in which an input port, a main port, an exhaust port, a ventilation path, and a relief valve are integrally included in a housing can be realized.

DESCRIPTION OF EMBODIMENTS

An exemplary embodiment according to an aspect of the present disclosure will be described below with reference to the drawings. The embodiment, which will be described below, does not unreasonably limit the scope of the present invention described in the claims, and not all the configurations in the description of the embodiment are essential as the solutions of the present invention. In the following description, terms indicating directions such as "upward", "downward", "left", and "right" are used for convenience of description and are not intended to describe how to use a ventilator 1 or a mode of use of the ventilator 1. The terms "first", "second", and "third" that are mentioned in the present specification and the claims are used as identification terms that distinguish different components in the present invention and the embodiment and are not used for indicating either a specific order or superiority. Consequently, larger ordinal number terms such as "fourth" that are not mentioned in the original specification may sometimes be used.

Overall Configuration of Ventilator 1

Figure 5:
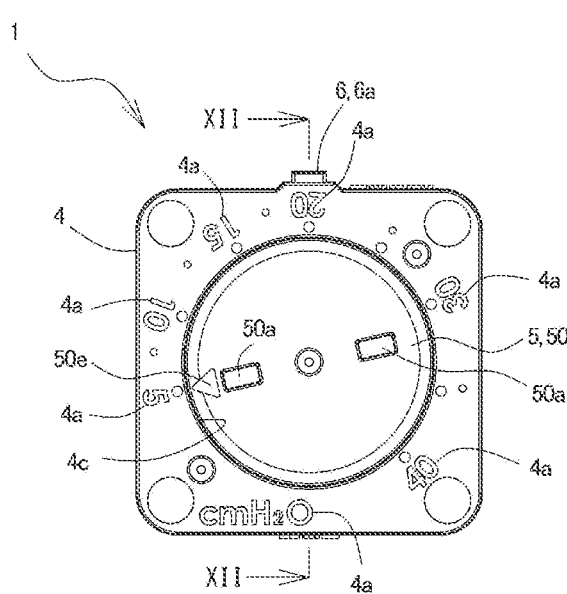
FIG. 5 is a plan view of the ventilator illustrated in FIG. 1.
Figure 6:
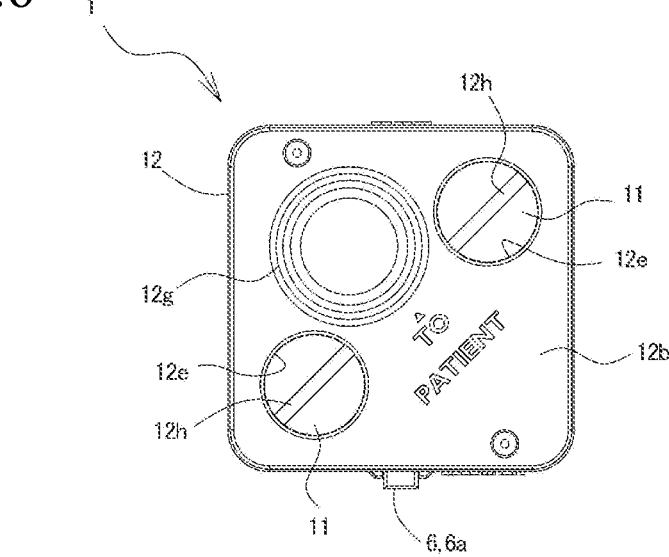
FIG. 6 is a bottom view of the ventilator illustrated in FIG. 1.
Figure 7:
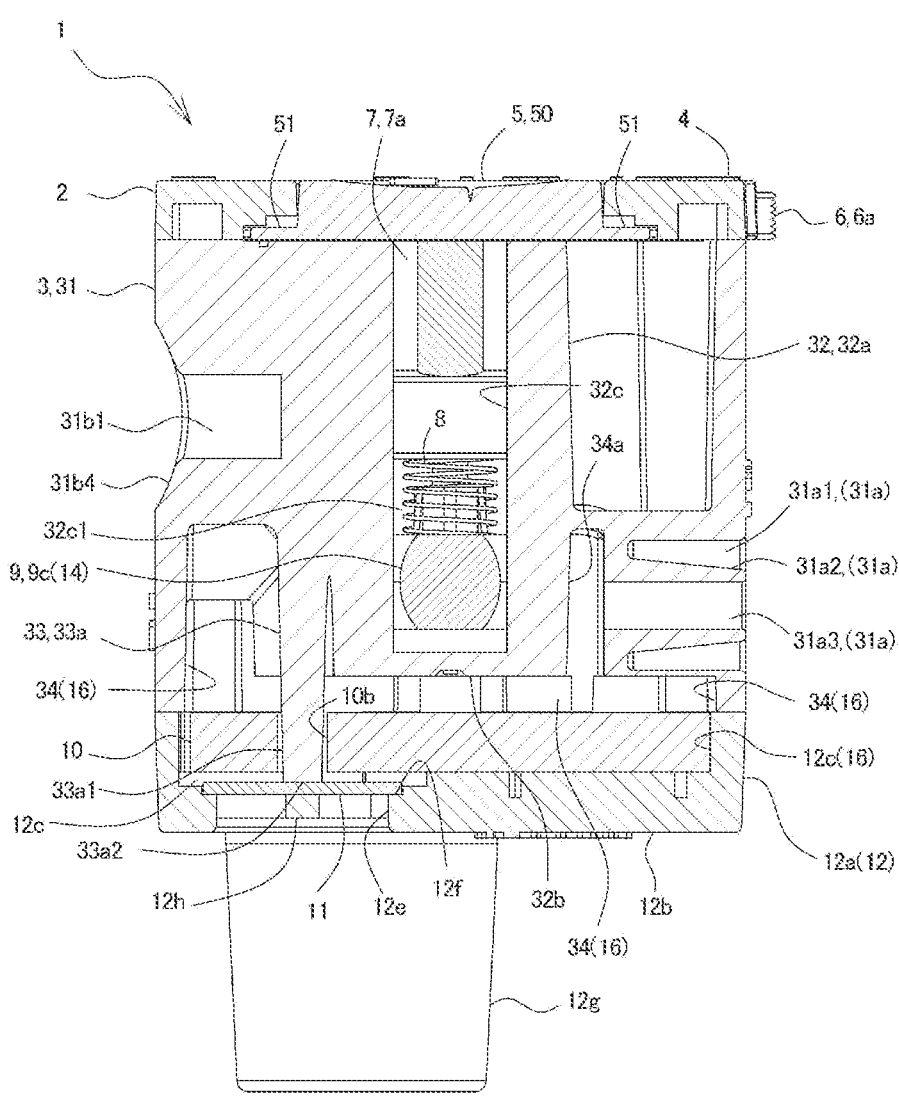
FIG. 7 is a sectional view taken along line VII-VII of FIG. 4.
Figure 8:
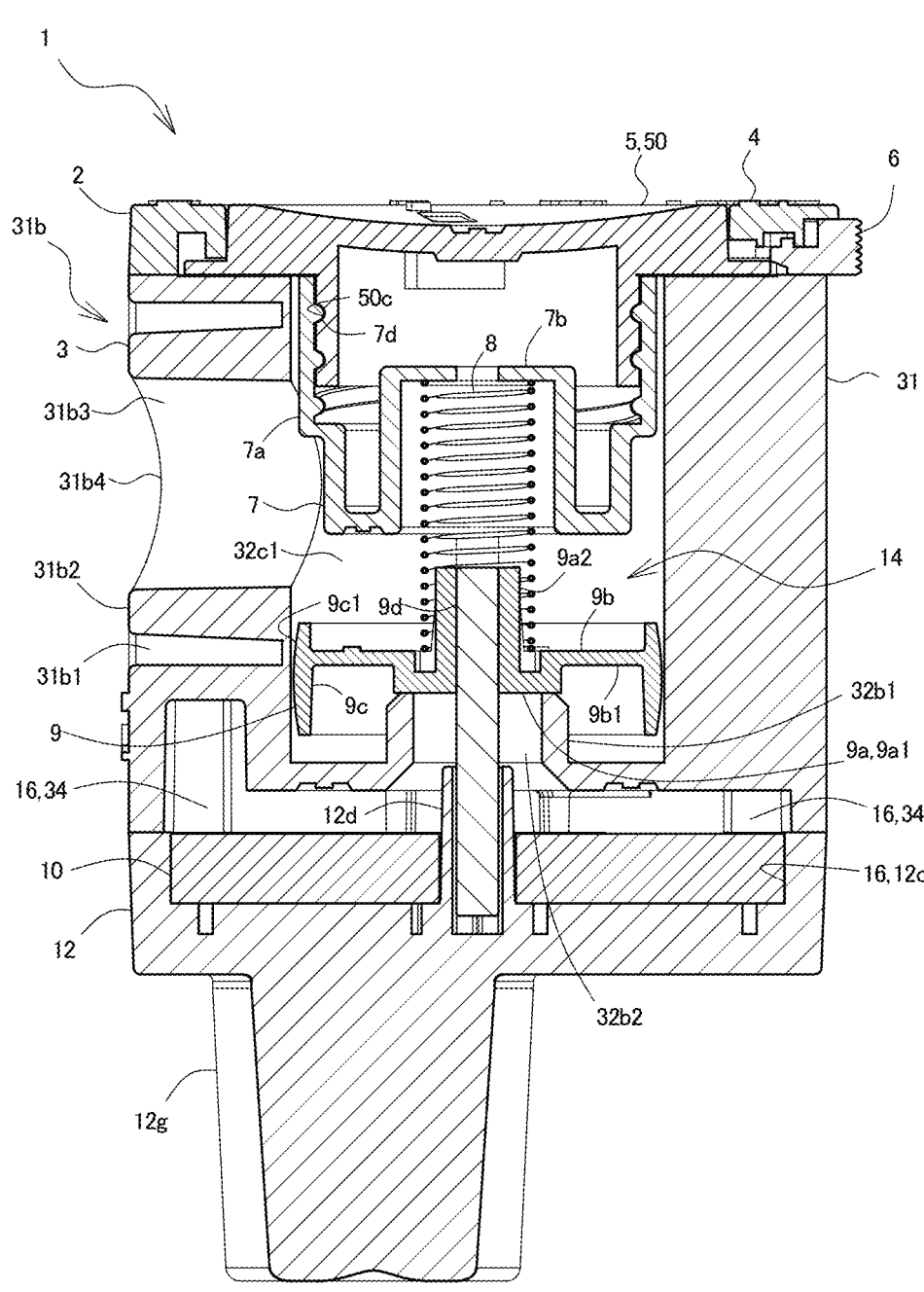
FIG. 8 is a sectional view taken along line VIII-VIII of FIG. 3.
Figure 9:
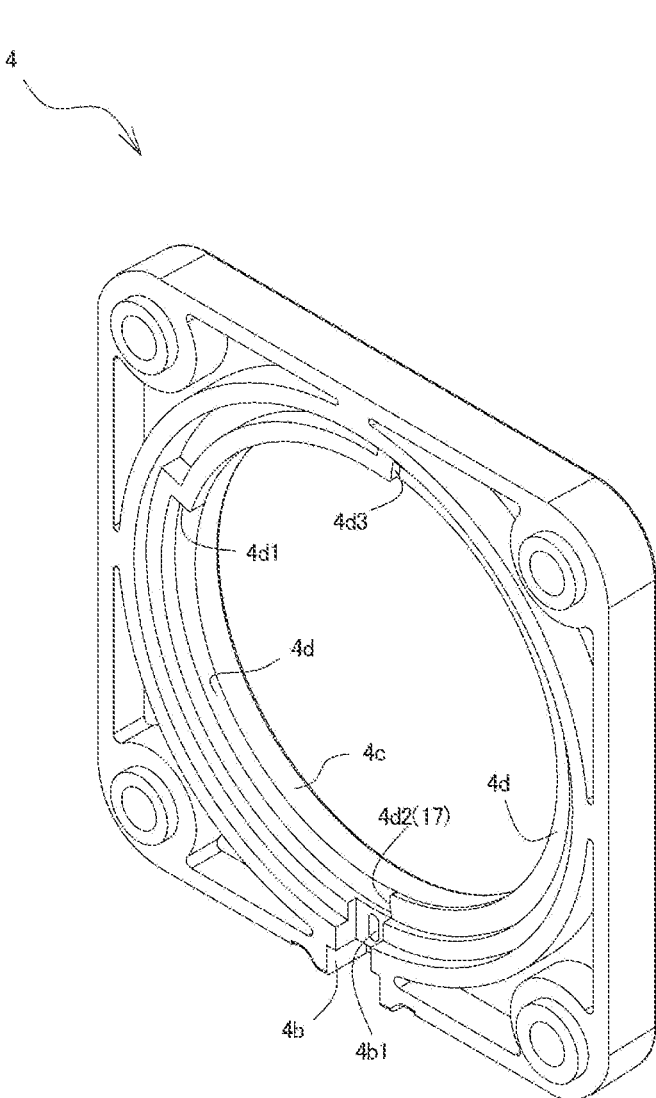
FIG. 9 is a rear perspective view of a dial cover of the ventilator illustrated in FIG. 1.
Figure 10:
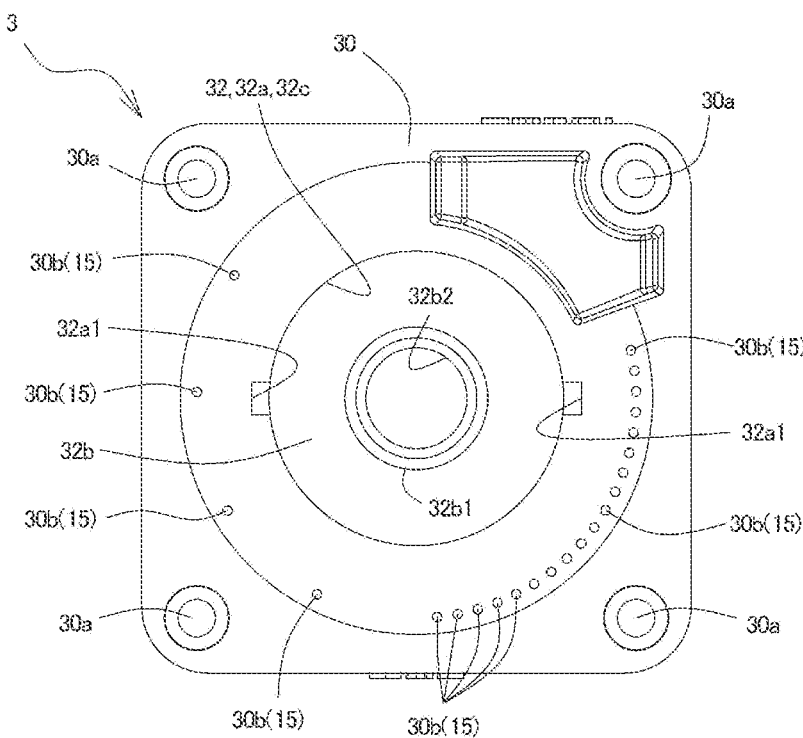
FIG. 10 is a plan view of a main body of the ventilator illustrated in FIG. 1.
Figure 11:
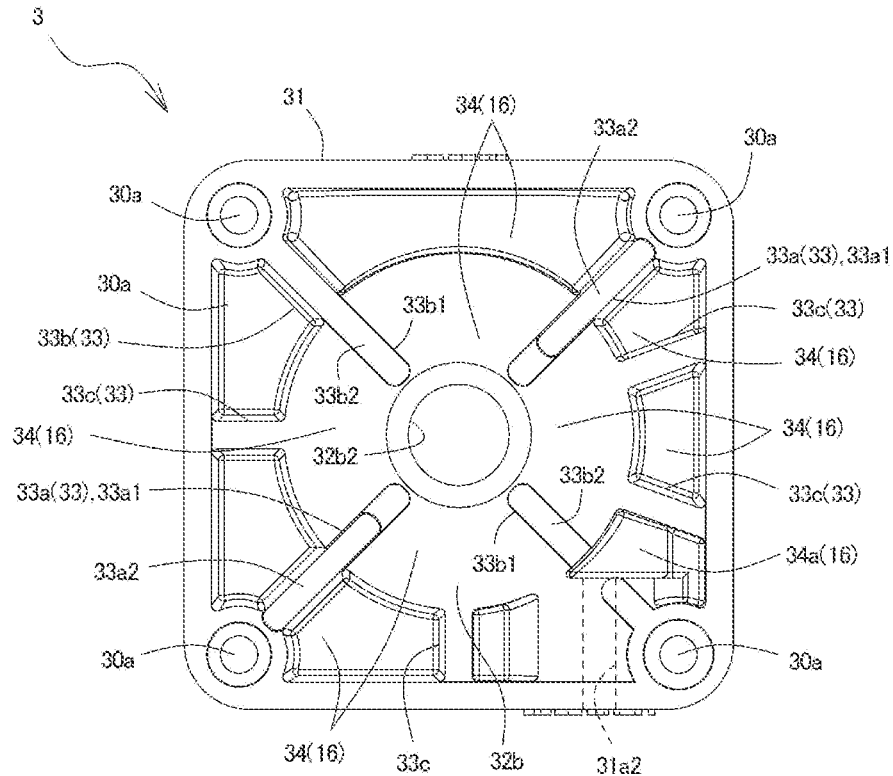
FIG. 11 is a bottom view of the main body of the ventilator illustrated in FIG. 1.
Figure 12:
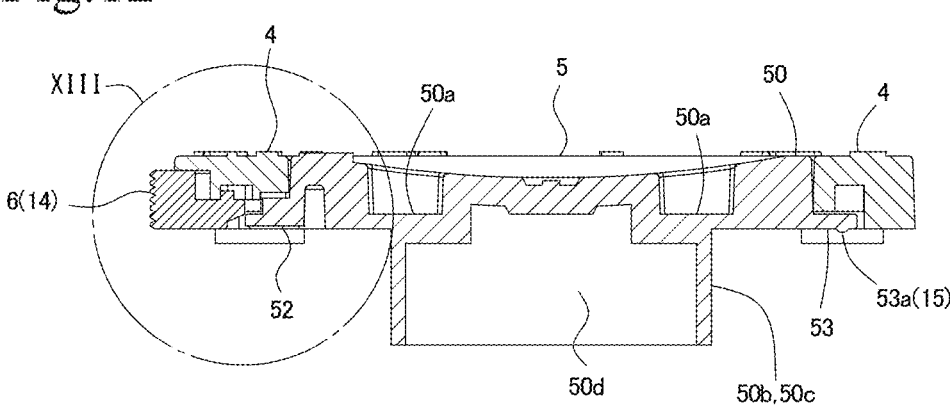
FIG. 12 is a sectional view illustrating the dial cover and a pressure setting dial, the sectional view being obtained by rotating a sectional view taken along line XII-XII of FIG. 5 by 90 degrees to the left.
Figure 13:
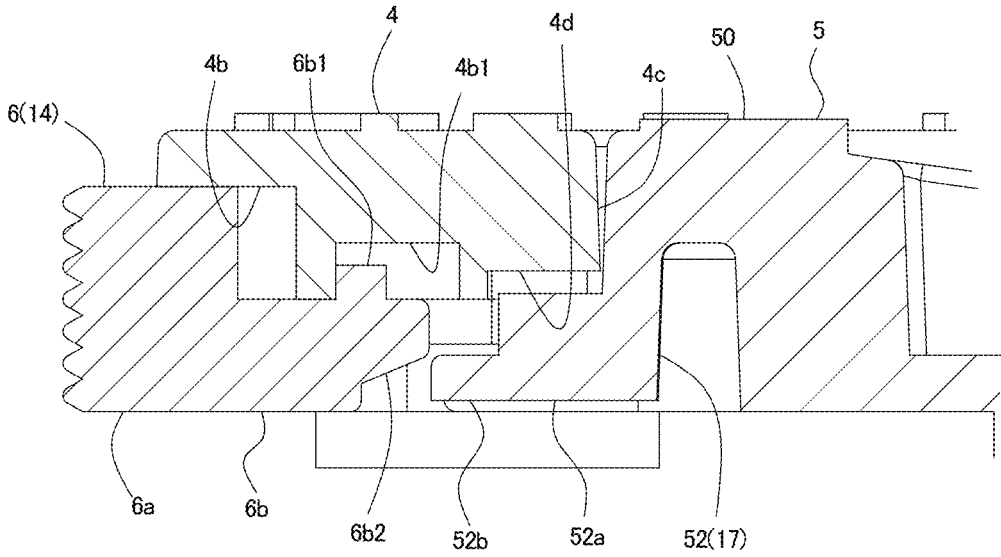
FIG. 13 is a partially enlarged view of a portion XIII in FIG. 12.

The ventilator 1 includes a housing 2. The housing 2 is formed by combining a plurality of components, and the overall shape of the housing 2 resembles a box-shaped polyhedron. In the present embodiment, the box-shaped polyhedron is a hexahedron. The outer peripheral surfaces (the front surface, the right-side surface, the rear surface, the left-side surface) and the top surface (FIG. 5) of the hexahedron are each formed of a flat surface with no significantly protruding geometrical element. Accordingly, the housing 2 is formed compact in its overall size, and when the ventilator 1 is placed on a table or the like, the ventilator 1 can be placed in a stable position so as not to roll off the table or the like. The bottom surface (FIG. 6) of the housing 2 has a main port 12g, which will be described later, protruding therefrom.

Description of Housing 2

Figure 14:
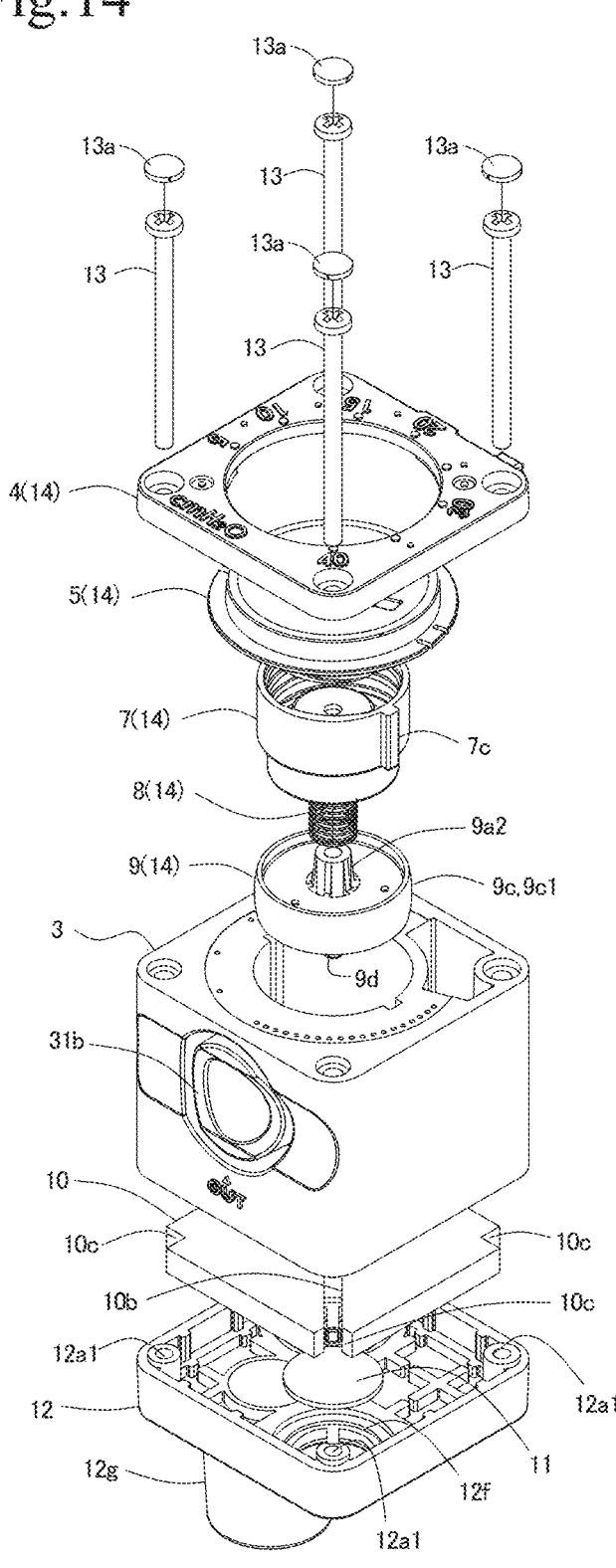
FIG. 14 is an exploded perspective view including the front surface, the right-side surface, and the flat surface of the ventilator illustrated in FIG. 1.
Figure 15:
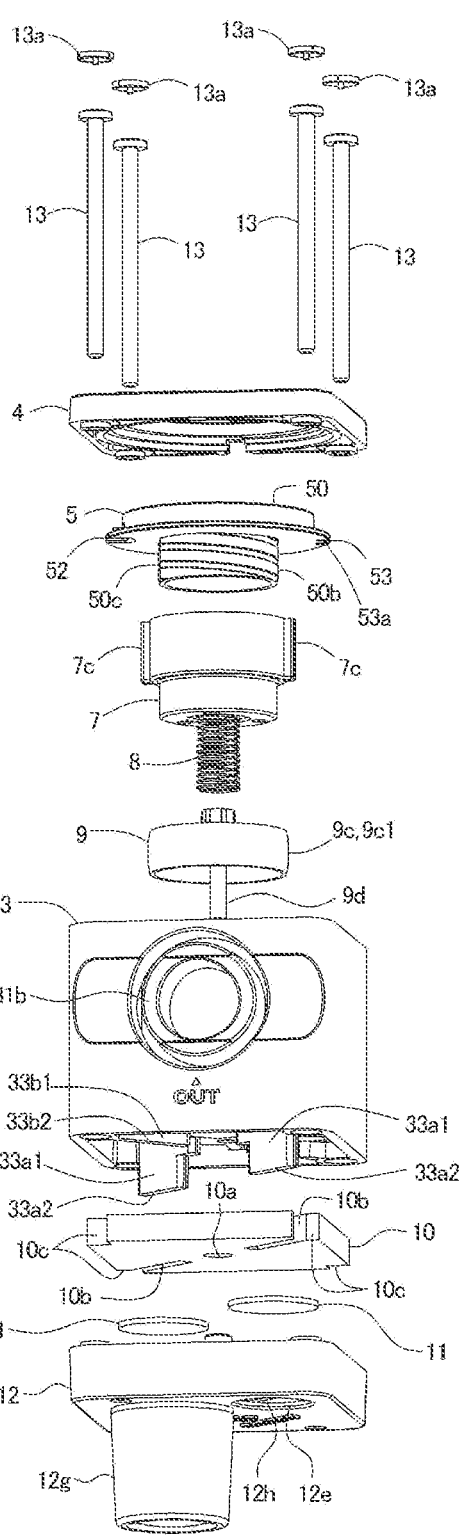
FIG. 15 is an exploded perspective view including the front surface, the right-side surface, and the bottom surface of the ventilator illustrated in FIG. 1.

As illustrated in FIG. 14 and FIG. 15, the housing 2 includes a main body 3, a dial cover 4, a pressure setting dial 5, an unlock button 6, a holder 7, a pressure setting spring 8, a valve body 9, a heat and moisture exchanger (HME) filter 10, valve films 11, a lid 12, and screws 13. The ventilator 1 is a new compact pulmonary resuscitator in which the above-mentioned components are integrally included in the housing 2. A relief valve 14 that is included in the ventilator 1 includes the dial cover 4, the pressure setting dial 5, the unlock button 6, the holder 7, the pressure setting spring 8, and the valve body 9.

Description of Main Body 3

The main body 3 is formed of a resin-molded body having the shape of a box. The main body 3 includes [1] an upper surface wall 30, [2] an outer peripheral wall 31, [3] a cylindrical accommodating unit 32 protruding inside the outer peripheral wall 31 from the rear surface of the upper surface wall 30, and [4] support walls 33 connecting the outer peripheral wall 31 and the accommodating unit 32.

[1] Upper Surface Wall 30

Hole ends of insertion holes 30a for the screws 13 are open at four corners of the upper surface wall 30. A cylindrical portion 32a of the accommodating unit 32 is open at the center of the upper surface wall 30. A plurality of engagement recesses 30b are formed around the opening of the cylindrical portion 32a. A small projection 53a that is formed on an engagement piece 53 of the pressure setting dial 5 (described later) engages into the engagement recesses 30b. In other words, when the pressure setting dial 5 is rotated in the clockwise direction, the small projection 53a engages into one of the engagement recesses 30b in such a manner as to provide a clicking sensation to an operator. This enables the operator to know that a set pressure value is changed by rotating the pressure setting dial 5. In addition, the small projection 53a engages into one of the engagement recesses 30b, so that the position of the pressure setting dial 5 can be maintained. The relief valve 14 of the ventilator 1 includes such a click generating unit 15 (the small projection 53a, the engagement recesses 30b). The engagement recesses 30b are formed at a one cmH$_2$O pitch from a minimum set pressure value (5 cmH$_2$O in the present embodiment) to an intermediate set pressure value (20 cmH$_2$O in the present embodiment). The engagement recesses 30b are formed at a five cmH$_2$O pitch from the intermediate set pressure value to a maximum set pressure value (45 cmH$_2$O in the present embodiment).

[2] Outer Peripheral Wall 31

The outer peripheral wall 31 is formed in a cylindrical shape, and in the present embodiment, the outer peripheral wall 31 is formed in a quadrangular cylindrical shape. An input port 31a and an exhaust port 31b are formed in the outer peripheral wall 31.

The input port 31a is a portion through which a gas to be inhaled by a patient is introduced into the housing 2. The input port 31a has an input-port recess 31a1 and a first connection pipe 31a2. The input-port recess 31a1 is recessed in a first outer surface 31c of the outer peripheral wall 31 toward the inside the housing 2. The first connection pipe 31a2 is formed inside the input-port recess 31a1. An introduction port 31a3 is open at the outer end of the first connection pipe 31a2. The inner end (a housing-side end) of the first connection pipe 31a2 is open to a ventilation path 16 (an input-side ventilation space 34a), which will be described later.

The first connection pipe 31a2 can be connected to a pipe for supplying a gas (e.g., air or a mixed gas of oxygen and air), an air or oxygen cylinder, an air compressor, or the like via an oxygen tube.

The first connection pipe 31a2 is formed in a tapered shape in such a manner that the outer diameter of the first connection pipe 31a2 increases in a direction from the outer end toward the inner end. Connection portions of oxygen tubes do not have a fixed standard, and there is also a type of tube that is individually used by being cut like a bubble tube. Since the first connection pipe 31a2 has a tapered shape, various tubes such as those mentioned above can be connected to the first connection pipe 31a2 regardless of their inner diameters.

An inspiratory primary-side connection object (a pipe or a connection port) can be inserted into the gap between the input-port recess 31a1 and the first connection pipe 31a2. Consequently, a connection portion in which the first connection pipe 31a2 and the inspiratory primary-side connection object are connected to each other can be protected against the action of an external force by being concealed in the input-port recess 31a1. Therefore, the inspiratory primary-side connection object can be prevented from becoming loose or disconnected due to unintentional contact of a person or an object with the connection portion.

The introduction port 31a3 of the first connection pipe 31a2 is disposed so as not to project outward from the first outer surface 31c of the outer peripheral wall 31. As a result, the first outer surface 31c of the outer peripheral wall 31, in which the input port 31a is formed, can be formed as a flat surface with no significantly protruding geometrical element. Thus, the outer peripheral wall 31 can be formed compact in its overall size, and the ventilator 1 can be placed on a table or the like in a stable position. In addition, since the input port 31a does not project, the risk of damaging or breaking the input port 31a when the ventilator 1 is dropped can be reduced.

The exhaust port 31b is a portion through which a gas or an exhaled gas is exhausted from the housing 2. The exhaust port 31b has an exhaust-port recess 31b1 and a second connection pipe 31b2. The exhaust-port recess 31b1 is recessed in a second outer surface 31d of the outer peripheral wall 31 toward the inside the housing 2. The second connection pipe 31b2 is formed inside the exhaust-port recess 31b1. The inner end (a housing-side end) of the second connection pipe 31b2 is open to a valve chamber 32c1, which will be described later.

The second connection pipe 31b2 can be inserted into, for example, a corrugated tube or the like. However, the second connection pipe 31b2 may be open without being connected to a corrugated tube or the like.

The second connection pipe 31b2 is formed in a tapered shape in such a manner that the outer diameter of the second connection pipe 31b2 increases in a direction from the outer end of the second connection pipe 31b2 toward the inner end. Corrugated tubes that are commercially available and that are connectable to the second connection pipe 31b2 are, for example, a corrugated tube having an inner diameter of 18 mm and a corrugated tube having an inner diameter of 22 mm, and the inner diameters of such corrugated tubes slightly vary depending on the manufacturer. Although such corrugated tubes have different inner diameters, the tapered shape of the second connection pipe 31*b*2 enables them to be fitted and reliably connected to the second connection pipe 31*b*2.

An exhaust secondary-side connection object (a corrugated tube or the like) can be inserted into the gap between the exhaust-port recess 31*b*1 and the second connection pipe 31*b*2. Consequently, a connection portion in which the second connection pipe 31*b*2 and the exhaust secondary-side connection object are connected to each other can be protected against the action of an external force by being concealed in the exhaust-port recess 31*b*1. Therefore, the exhaust secondary-side connection object can be prevented from becoming loose or disconnected due to unintentional contact of a person or an object with the connection portion.

An outlet 31*b*3 of the second connection pipe 31*b*2 is disposed so as not to project outward from the second outer surface 31*d* of the outer peripheral wall 31. As a result, the second outer surface 31*d* of the outer peripheral wall 31, in which the exhaust port 31*b* is formed, can be formed as a flat surface with no significantly protruding geometrical element. Thus, the outer peripheral wall 31 can be formed compact in its overall size, and the ventilator 1 can be placed on a table or the like in a stable position.

An end surface of the outlet 31*b*3 of the second connection pipe 31*b*2 does not have a shape such as that obtained by directly cutting it in a radial direction, and the outlet 31*b*3 has a curved recess 31*b*4 that is recessed toward the inside of the housing 2. The curved recess 31*b*4 has a curved shape such as that obtained by cutting off the end surface of the outlet 31*b*3 in a direction from the outer end side toward the inside of the housing 2 into an arc shape. Such a curved shape is formed so as to follow, for example, the shape of the ball of a thumb. For example, while using the ventilator 1, there is a case where a foreign matter such as sputum found in the trachea, a bronchus, or a lung is desired to be removed by guiding the foreign matter toward the upper respiratory tract side in order to help a patient breathe easier. In such a case, the outlet 31*b*3 is completely closed with a thumb so as to make the patient to keep inhaling, and the patient's lungs are caused to inflate such that the airway pressure increases momentarily. Next, the thumb is released, so that the relief valve 14 is opened, and a gas is exhausted through the exhaust port 31*b*. Then, the airway pressure, which has increased momentarily, is reduced, and the inflated lungs deflate momentarily, so that the foreign matter can be guided toward the upper respiratory tract side. When such a guiding treatment for a foreign matter is performed, since the outlet 31*b*3 has the curved recess 31*b*4, the outlet 31*b*3 can be closed by putting, for example, the ball of a thumb properly along the curved recess 31*b*4, so that the guiding treatment can be easily and reliably performed.

Ventilation grooves 31*e* are formed in the second outer surface 31*d*, which has the exhaust port 31*b*, in such a manner as to communicate with the outlet 31*b*3 and to extend to the outer end of the second outer surface 31*d*. The ventilation grooves 31*e* are each formed of a curved concave surface and extend from both sides of the exhaust port 31*b* toward the outer end of the second outer surface 31*d*. By forming the ventilation grooves 31*e* such as those described above, for example, even if a wall surface, a part of the human body, a piece of clothing, a pillow, or the like comes into contact with the outlet 31*b*3 and almost blocks the outlet 31*b*3 unintentionally, an exhaust path can be maintained by the ventilation grooves 31*e*, and the ventilator 1 can be safely used without completely stopping exhaustion of a gas. Note that, although the ventilation grooves 31*e* are provided at the opposite sides of the exhaust port 31*b*, the ventilation groove 31*e* may be provided only one side of the exhaust port 31*b*.

[3] Accommodating Unit 32

The accommodating unit 32 includes the cylindrical portion 32*a* and a bottom-surface portion 32*b*. Some of the components of the relief valve 14 including the holder 7, the pressure setting spring 8, and the valve body 9 are arranged in an accommodating space 32*c* that is formed and defined by the cylindrical portion 32*a* and the bottom-surface portion 32*b*. In this manner, the accommodating unit 32 enables the compact arrangement of the components of the relief valve 14.

The inner end (the housing-side end) of the second connection pipe 31*b*2 of the exhaust port 31*b* is open at the inner peripheral surface of the cylindrical portion 32*a*. The inner peripheral surface of the cylindrical portion 32*a* has guides 32*a*1 that guide the holder 7 such that the holder 7 moves along the central axis direction of the accommodating unit 32. The guides 32*a*1 are formed of a pair of grooves into which a pair of guide projections 7*c* that are formed on the outer peripheral surface of the holder 7 are inserted. Thus, the guide projections 7*c* are guided along the guides 32*a*1, so that the holder 7 can move, in a balanced position, inside the accommodating unit 32 along the central axis direction.

The bottom-surface portion 32*b* includes a valve seat 32*b*1 and has a valve hole 32*b*2. The valve seat 32*b*1 is formed in a cylindrical shape protruding toward the accommodating space 32*c* and has a diameter smaller than the diameter of the bottom-surface portion 32*b*. The valve hole 32*b*2 is formed as the inner peripheral surface of the valve seat 32*b*1, and is formed as a through hole extending through the bottom-surface portion 32*b*.

The accommodating space 32*c* has the valve chamber 32*c*1. The valve chamber 32*c*1 is formed of a space between the bottom-surface portion 32*b* and the holder 7, and a lower portion of the pressure setting spring 8 and the valve body 9 are located in the valve chamber 32*c*1. The valve body 9 is movable inside the valve chamber 32*c*1 in the vertical direction. The space height of the valve chamber 32*c*1 varies in accordance with the position of the holder 7 which is movable in the central axis direction of the accommodating unit 32 (the position of the bottom surface of the holder 7 facing the valve chamber 32*c*1). The valve chamber 32*c*1 is formed at a position where the valve chamber 32*c*1 is in constant communication with the above-mentioned exhaust port 31*b*.

[4] Support Walls 33

The support walls 33 are formed at a plurality of positions so as to connect the outer peripheral wall 31 and the accommodating unit 32 to each other. First ventilation spaces 34 are formed between the adjacent support walls 33. One of the plurality of first ventilation spaces 34 is formed as the input-side ventilation space 34*a*. The inner end (the housing-side end) of the first connection pipe 31*a*2 of the input port 31*a* is open to the input-side ventilation space 34*a*. A gas that flows into the ventilator 1 from the input port 31*a* flows into the input-side ventilation space 34*a* first, and then, the gas flows into the first ventilation spaces 34.

The support walls 33 include first support walls 33*a*, second support walls 33*b*, and third support walls 33*c*. The first support walls 33*a* each include a first leg portion 33*a*1 protruding downward, and the second support walls 33*b* each include a second leg portion 33*b*1 protruding downward. The third support walls 33*c* are formed so as not to project downward from the bottom-surface portion 32*b* of the accommodating unit 32, and their positions are at the same level as the position of the bottom-surface portion 32*b*.

The first leg portions 33*a*1 are formed at opposite sides of the valve hole 32*b*2 along a first diagonal line of the housing 2 such that the valve hole 32*b*2 is located between the first leg portions 33*a*1. The first leg portions 33*a*1 are each elongated beyond the lower end of the outer peripheral wall 31. The ends of the first leg portions 33*a*1 serve as first holding portions 33*a*2 that press the valve films 11 by passing through the HME filter 10. Thus, the HME filter 10 is reliably held by the first leg portions 33*a*1.

The second leg portions 33*b*1 are formed at opposite sides of the valve hole 32*b*2 along a second diagonal line of the housing 2 such that the valve hole 32*b*2 is located between the second leg portions 33*b*1. The ends of the second leg portions 33*b*1 serve as second holding portions 33*b*2 that press the HME filter 10. Thus, the HME filter 10 does not flap when the patient inhales, and the HME filter 10 can be reliably maintained in its arranged state.

In the housing 2, the HME filter 10 is positioned below the support walls 33. In a state where the second holding portions 33*b*2 of the second leg portions 33*b*1 are in contact with the HME filter 10, a gap is formed between the HME filter 10 and the bottom-surface portion 32*b* of the accommodating unit 32. This gap forms the first ventilation spaces 34, and the first ventilation spaces 34 forms the ventilation path 16.

Description of Dial Cover 4

The dial cover 4 is formed of a resin-molded body and attached to the upper surface wall 30 of the main body 3, and the pressure setting dial 5 is rotatably held by the dial cover 4.

Display portions 4*a* are formed on the front surface of the dial cover 4 so as to three-dimensionally display a plurality of numbers that correspond to pressure values to be set and a unit. The relief valve 14 of the present embodiment operates as an APL valve. As an example, the display portions 4*a* are formed in such a manner as to three-dimensionally project from the front surface of the dial cover 4. However, the display portions 4*a* may be formed in such a manner as to be three-dimensionally recessed in the front surface. Since the display portions 4*a* are formed as portions of the resin-molded body in this manner, the displayed numbers and the displayed unit will not disappear over time. In the present embodiment, one of the display portions 4*a* is formed so as to display "5" as the minimum set pressure value, and the other display portions 4*a* are formed so as to display "10", "15", "20", "30", "40", and "cmH₂O" that is the unit of the set pressure value.

An arrangement recess 4*b* for the unlock button 6 is formed in the rear surface of the dial cover 4. The arrangement recess 4*b* has a guide recess 4*b*1 that guides movement of the unlock button 6.

The rear surface of the dial cover 4 has a rotation guide 4*d* formed around a circular arrangement opening 4*c* in which a dial main body 50 of the pressure setting dial 5 is disposed. The rotation guide 4*d* is a portion that guides rotation of a flange 51 of the pressure setting dial 5, which will be described later, and prevents the pressure setting dial 5 from coming off. The rotation guide 4*d* includes a first contact receiving portion 4*d*1 positioned so as to correspond to the position of the display portion 4*a* displaying "5", a second contact receiving portion 4*d*2 positioned so as to correspond to the position of the display portion 4*a* displaying "20", and a third contact receiving portion 4*d*3 positioned so as to correspond to the position of "45" that is not displayed by any of the display portions 4*a* and that is not present on the front surface of the dial cover 4.

The pressure setting dial 5 is freely rotatable between the first contact receiving portion 4*d*1 and the second contact receiving portion 4*d*2. Rotation of the pressure setting dial 5 is stopped as a result of a stopper 52 coming into contact with the first contact receiving portion 4*d*1, and the minimum set pressure value "5" is set at the stop position. Rotation of the pressure setting dial 5 is stopped as a result of the stopper 52 coming into contact with the second contact receiving portion 4*d*2, and the intermediate set pressure value "20" is set at the stop position. Note that the minimum, intermediate, and maximum set pressure values in the present embodiment are examples and may be different values.

In order to set a pressure value larger than the intermediate set pressure value "20", the stopper 52 needs to climb over a step of the second contact receiving portion 4*d*2. In order to enable the stopper 52 to climb over the step, an operator pushes the unlock button 6 toward the center of the pressure setting dial 5 so as to push the stopper 52 down. As a result, the stopper 52 can climb over the step. In a state where the stopper 52 has climbed over the step, the pressure setting dial 5 is rotated, so that the pressure setting dial 5 can be further rotated to the maximum set pressure value "45".

In this manner, free rotation of the pressure setting dial 5 is restricted at predetermined set pressure values, and a rotation unlock mechanism 17 (the second contact receiving portion 4*d*2, the stopper 52) for setting a pressure value larger than the predetermined set pressure values is provided, so that the airway pressure can be prevented from being accidentally set too high.

Description of Pressure Setting Dial 5

The pressure setting dial 5 is formed of a resin-molded body having a disc-like shape and includes the dial main body 50, the flange 51, the stopper 52, and the engagement piece 53.

Two key holes 50*a* is formed in the front surface of the dial main body 50, and a pressure setting key 18 that is used for a rotary operation of the dial main body 50 is inserted into the key holes 50*a*. The pressure setting key 18 will be described later. A protruding cylinder 50*b* is formed on the rear surface of the dial main body 50, and an external thread 50*c* that engages with an internal thread 7*d* of the holder 7 is formed on the outer peripheral surface of the protruding cylinder 50*b*. The external thread 50*c* and the internal thread 7*d* are each a double-start thread, and the rotation accuracy of the pressure setting dial 5 is improved. The external thread 50*c* and the internal thread 7*d* are each formed as a pressure setting thread.

A spring accommodating portion 50*d* is formed inside the protruding cylinder 50*b*, and an upper end portion of the pressure setting spring 8 is inserted into the spring accommodating portion 50*d*.

The flange 51 is disposed so as to face the rotation guide 4*d* of the dial cover 4, which has been mentioned above. In the flange 51, the stopper 52 and the engagement piece 53 are formed in cutout portions formed by cutting out the flange 51.

The stopper 52 is formed as a protrusion extending from the side surface of the dial main body 50 in a cantilever manner. The stopper 52 includes a thick portion 52*a* and a thin portion 52*b*. Upon a rotary operation of the pressure setting dial 5, the stopper 52 comes into contact with one of the first contact receiving portion 4*d*1, the second contact receiving portion 4*d*2, and the third contact receiving portion 4*d*3, which have been mentioned above, so that the rotation amount can be controlled. The stopper 52 is displaceable in the height direction of the flange 51 while a base end of the thick portion 52a (an end of the thick portion 52a closer to the dial main body 50) serves as a fulcrum. Thus, when the unlock button 6 is pushed, the stopper 52 is displaced downward and climbs over the step of the second contact receiving portion 4d2, so that the pressure setting dial 5 can be released form a locked state in which its rotation is restricted.

A set-pressure-value indication portion 50e is formed on the front surface of the dial main body 50 and positioned so as to face the stopper 52. In the present embodiment, although the set-pressure-value indication portion 50e is three-dimensionally formed as a triangular symbol, the set-pressure-value indication portion 50e may have a different shape as long as a set pressure value can be determined. Note that, although the set-pressure-value indication portion 50e has a three-dimensionally projecting shape as an example, the set-pressure-value indication portion 50e may have a three-dimensionally recessed shape.

The engagement piece 53 is formed as a protrusion extending from the side surface of the dial main body 50 in a cantilever manner. Accordingly, also the engagement piece 53 is displaceable in the height direction of the flange 51 while a base end of the engagement piece 53 (an end of the engagement piece 53 closer to the dial main body 50) serves as a fulcrum. The small projection 53a is formed on the rear surface of the engagement piece 53. The small projection 53a engages into one of the engagement recesses 30b of the upper surface wall 30 of the main body 3, which has been mentioned above, so that a clicking sensation can be provided upon a rotary operation of the pressure setting dial 5. As a result of the engagement piece 53 being deformed and displaced in the height direction of the flange 51, the small projection 53a engages into or is released from one of the engagement recesses 30b.

Description of Unlock Button 6

The unlock button 6 serves as an "unlocking unit" and includes a pushing-operation portion 6a and a push portion 6b. The pushing-operation portion 6a is disposed in the arrangement recess 4b of the dial cover 4 in such a manner as to slightly project from the outer peripheral surface of the dial cover 4. Thus, a user can easily perceive that the pushing-operation portion 6a is a portion to be pushed.

As described above, the arrangement recess 4b has the guide recess 4b1, and a guide projection 6b1 of the push portion 6b is located in the guide recess 4b1. This enables the unlock button 6 to smoothly move forward and rearward in a radial direction toward the center of the pressure setting dial 5, and the unlock button 6 can be prevented from coming off the housing 2. The push portion 6b includes an inclined-surface portion 6b2. The inclined-surface portion 6b2 obliquely comes into contact with the thin portion 52b of the stopper 52 of the pressure setting dial 5, which in turn leads to a smooth displacement of the stopper 52 in the downward direction.

Description of Holder 7

The holder 7 includes a holder main body 7a having a cylindrical shape and a cylindrical protruding portion 7b protruding in a direction from the bottom surface of the holder main body 7a toward the upper end of the holder main body 7a.

The guide projections 7c are formed on the outer peripheral surface of the holder main body 7a. The guide projections 7c are guided along the guides 32a1 of the cylindrical portion 32a of the accommodating unit 32, so that the holder 7 can move, in a balanced position, inside the accommodating unit 32 along the central axis direction.

The internal thread 7d that engages with the external thread 50c of the pressure setting dial 5 is formed in the inner peripheral surface of the holder main body 7a. The internal thread 7d engages with the external thread 50c by rotating the pressure setting dial 5 in the clockwise direction, so that the holder main body 7a is moved downward. In this case, the compression amount by which the holder 7 compresses the pressure setting spring 8 increases. Thus, elastic deformation of the pressure setting spring 8 requires a higher pressing force, and the pressure for opening the valve body 9 also increases. Contrary to this, the holder main body 7a is moved upward by rotating the pressure setting dial 5 in the counterclockwise direction, so that the pressure for opening the valve body 9 is reduced.

The upper end portion of the pressure setting spring 8 is inserted into the cylindrical protruding portion 7b so as to be located inside the cylindrical protruding portion 7b.

Description of Pressure Setting Spring 8

The pressure setting spring 8 is a compression-coil spring made of a metal. As mentioned above, the upper end portion of the pressure setting spring 8 is inserted into and held in the cylindrical protruding portion 7b of the holder 7. On the other hand, a lower end portion of the pressure setting spring 8 is fitted over and held by a cylindrical protrusion 9a2 of the valve body 9. Note that, although the pressure setting spring 8 of the present embodiment is made of a metal, the pressure setting spring 8 may be formed of a resin-molded body for the purpose of reducing the manufacturing costs or enabling the pressure setting spring 8 to be taken into an MRI room where metal objects cannot be taken into.

Description of Valve Body 9

The valve body 9 includes a base 9a, an annular portion 9b, a cylindrical surrounding wall 9c, and a valve shaft 9d.

The base 9a has a disc-like shape, and when the valve body 9 is in a closed state, the base 9a is in contact with the valve seat 32b1 so as to close the valve hole 32b2. A portion of the base 9a that is exposed in the valve hole 32b2 when the valve body 9 is in the closed state is formed as a first pressure-receiving surface portion 9a1 that receives the pressure of a gas to be inhaled and the pressure of an exhaled gas. The upper surface of the base 9a has the cylindrical protrusion 9a2 inserted in the lower end portion of the pressure setting spring 8.

The annular portion 9b is formed in a ring-like shape protruding outward from the outer peripheral surface of the base 9a. When the valve body 9 is in the closed state, the annular portion 9b serves as a second pressure-receiving surface portion 9b1 that receives the pressure of a gas that flows thereinto.

The cylindrical surrounding wall 9c is formed at the outer periphery end of the annular portion 9b. An inner peripheral surface portion of the cylindrical surrounding wall 9c that is contiguous to the second pressure-receiving surface portion 9b1 is formed as a portion that receives, together with the second pressure-receiving surface portion 9b1, the gas that flows to the second pressure-receiving surface portion 9b1. The cylindrical surrounding wall 9c also protrudes on the side on which the upper surface of the annular portion 9b is present so as to achieve a balance of the entire valve body 9 that performs opening and closing operations by receiving the pressure of the gas.

The cylindrical surrounding wall 9c has a spherical outer peripheral surface 9c1 having upper and lower ends that are curved toward the center axis of the valve body 9. Accordingly, even if the valve body 9 obliquely tilts when it performs the opening and closing operations, the valve body 9 can properly perform the opening and closing operations without the upper end edge and the lower end edge of the cylindrical surrounding wall 9*c* becoming stuck in the valve chamber 32*c*1. In addition, a ventilation gap is formed between the spherical outer peripheral surface 9*c*1 and the valve chamber 32*c*1, and the valve body 9 can be smoothly displaced.

The valve shaft 9*d* is formed of a metal bar made of a stainless steel or the like and integrated with the base 9*a*. In the present embodiment, the valve shaft 9*d* and the base 9*a* are formed into an integrally molded body by insert molding. With this configuration, the valve shaft 9*d* and the valve body 9 can be firmly integrated with each other, and problems such as displacement of the valve shaft 9*d* and separation of the valve shaft 9*d* will not occur, so that the durability and the safety of the valve body 9 can be improved.

The valve shaft 9*d* is disposed along the central axis of the valve body 9, and the upper end of the valve shaft 9*d* slightly projects from the upper surface of the cylindrical protrusion 9*a*2. The lower end of the valve shaft 9*d* is inserted in a bearing portion 12*d* of the lid 12, which will be described later. As will be described later, the lower end of the valve shaft 9*d* is held so as not to come off from the bearing portion 12*d* even if the valve body 9 is opened to the maximum extent when the valve body 9 performs the opening and closing operations, and the valve shaft 9*d* accurately moves up and down by being guided by the bearing portion 12*d*. As a result of the lower end of the valve shaft 9*d* being inserted and held in the bearing portion 12*d* in the manner described above, the durability of the valve body 9 is improved so that the valve body 9 can continue to perform accurate opening and closing operations.

The valve body 9 operates in the following manner. The pressure of the gas (the gas to be inhaled or the exhaled gas) is exerted on the first pressure-receiving surface portion 9*a*1, and when the pressure exceeds the valve opening pressure of the valve body 9 (the set pressure of the pressure setting spring 8), the valve body 9 is displaced away from the valve seat 32*b*1. As a result, the valve body 9 is opened. Then, the second pressure-receiving surface portion 9*b*1 and the inner surface of the cylindrical surrounding wall 9*c* receives the pressure of the gas flowing in from the valve seat 32*b*1, so that the valve body 9 is further displaced away from the valve seat 32*b*1. This increases the pressure-receiving area of the valve body 9 that receives the pressure of the gas. Thus, the valve body 9 keeps receiving the pressure in the increased pressure-receiving area while the pressure is released as a result of the gas flowing out through the ventilation gap, so that the valve-opening state of the valve body 9 can be stably maintained while suppressing a rapid pressure reduction.

Description of Heat and Moisture Exchanger Filter 10

The HME filter 10 is formed in a polygonal shape and has an insertion hole 10*a* formed at the center thereof and grooves 10*b* through which the above-mentioned first leg portions 33*a*1 of the first support walls 33*a* extend. As will be described later, the HME filter 10 is positioned between the main port 12*g* through which the gas to be inhaled and the exhaled gas flow and the exhaust port 31*b*. Thus, when the exhaled gas passes through the HME filter 10, the HME filter 10 can capture the heat and the moisture of the exhaled gas. The gas to be inhaled is warmed and humidified by passing through the HME filter 10, so that the airway of a patient can be prevented from becoming dry. In addition, even if a foreign matter such as vomit flows backward from the main port 12*g*, the HME filter 10 can receive the foreign matter so as to stop the flow of the foreign matter without hindering the normal operation of the relief valve 14.

For example, in the case of obtaining a plurality of the HME filters 10 from a sheet-shaped filter sheet member, if each of the HME filters 10 has a circular shape, portions of the filter sheet member will go to waste, that is, there will be material loss. In contrast, since the HME filter 10 has a polygonal shape, the loss at the time of material cutting can be reduced. This is also the reason why the housing 2 has a quadrangular shape.

Description of Valve Films 11 (Spontaneous-Breathing Valve)

The valve films 11 are each formed of a rubber-like elastic body made of a natural rubber, a synthetic rubber, thermoplastic elastomer, thermosetting elastomer, or the like. Normally, the valve films 11 hermetically seal spontaneous-breathing openings 12*e* that are formed in the lid 12. The valve films 11 are turned up by the inspiratory pressure at which a patient spontaneously breathes, so that the valve films 11 each function as a "spontaneous-breathing valve" that allows communication between the ventilation path 16 of the housing 2 and the outside of the housing 2. If a patient who is unconscious and is under mechanical ventilation awakes, the patient will have difficulty inhaling with the mechanical ventilation, and the patient may sometimes suddenly and spontaneously take a deep breath. Even in such a case, since each of the valve films 11 functions as the spontaneous-breathing valve, unexpected spontaneous breathing can also be managed, and the patient can breathe safely.

Description of Lid 12

The lid 12 is formed of a resin-molded body and assembled to the bottom surface of the main body 3. The lid 12 has an outer peripheral wall 12*a* and a bottom-surface portion 12*b*. A space that is formed and defined by the outer peripheral wall 12*a* and the bottom-surface portion 12*b* serves as a second ventilation space 12*c*. By assembling the lid 12 to the main body 3, the first ventilation spaces 34 of the main body 3 and the second ventilation space 12*c* of the lid 12 are integrated into one space that serves as the ventilation path 16.

The above-mentioned HME filter 10 is disposed in the second ventilation space 12*c*. A cylindrical bearing portion 12*d* is formed in such a manner as to project from the bottom-surface portion 12*b* and inserted in the insertion hole 10*a* of the HME filter 10, so that the HME filter 10 can be easily positioned at the center. Cylindrical screw holes 12*a*1 into which the screws 13 are screwed are formed at four corners of the outer peripheral wall 12*a*. Recessed positioning portions 10*c* that are formed at four corners of the HME filter 10 are aligned with their respective cylindrical screw holes 12*a*1, so that the HME filter 10 can be easily accommodated in the second ventilation space 12*c*, which is surrounded by the outer peripheral wall 12*a*. Then, the screws 13 are screwed into the screw holes 12*a*1, so that the ventilator 1 is assembled. Sealing portions 13*a* are arranged on the heads of the screws 13 such that the ventilator 1 cannot be disassembled by removing the screws 13. This is because, if the ventilator 1 is disassembled by removing the screws 13, there is a possibility that the ventilator 1 may not be able to exhibit its initial performance.

The spontaneous-breathing openings 12*e*, arrangement recesses 12*f* for the valve films 11, and the main port 12*g* are formed in the bottom-surface portion 12*b*.

In the present embodiment, the two spontaneous-breathing openings 12*e* are formed. The spontaneous-breathing openings 12e are each formed as a single opening, and the arrangement recesses 12f for the valve films 11 are each formed at the inner opening edge of one of the spontaneous-breathing openings 12e. Each of the arrangement recesses 12f is formed as an annular step surface having a height equivalent to the thickness of one of the valve films 11, and each of the valve films 11 is positioned and accommodated in the corresponding arrangement recess 12f such that the whole outer peripheral edge of the valve film 11 can be brought into close contact with the arrangement recess 12f. In each of the spontaneous-breathing openings 12e, a support portion 12h is provided in such a manner as to extend across the spontaneous-breathing opening 12e in a radial direction of the spontaneous-breathing opening 12e. Each of the support portions 12h is located in the corresponding spontaneous-breathing opening 12e and supports one of the valve films 11, and each of the valve films 11 is reliably held by the corresponding support portion 12h so as not to come off to the outside. Each of the support portions 12h can be fixed to the corresponding valve film 11 with an adhesive or the like or by thermal welding or ultrasonic welding. Fixing them by thermal welding or ultrasonic welding enables portions in each of which one of the support portions 12h and the corresponding valve film 11 are fixed together to have a fixing structure that is safer for a patient.

The valve films 11 arranged in the spontaneous-breathing openings 12e each have a first surface that is an outer surface supported by the corresponding support portion 12h and the corresponding arrangement recess 12f and a second surface that is an inner surface supported by the HME filter 10 and the first holding portions 33a2 of the first leg portions 33a1. The support portions 12h are positioned so as to overlap the first holding portions 33a2 in the thickness direction of the HME filter 10, and thus, the valve films 11 can be reliably sandwiched so as not to be displaced or come off.

When the valve films 11, which are arranged in the manner described above, are opened, portions of the valve films 11 that are not in contact with the support portions 12h are turned up so as to open the spontaneous-breathing openings 12e. In this case, the valve films 11 are turned up so as to elastically deform the HME filter 10. In other words, in a state where the valve films 11 are closed, non-restrained portions of the valve films 11 that are not fixed to the support portions 12h are pressed down by the HME filter 10 so as not to be turned up, and the spontaneous-breathing openings 12e can be closed with certainty.

The main port 12g is formed as a cylindrical tube protruding outward from the bottom surface of the lid 12. The main port 12g can be connected to, for example, a connection port of a resuscitation mask that is worn on a patient, a connection port of a corrugated tube that is connected to a resuscitation mask, a nasal or oral endotracheal intubation tube, a tracheostomy tube, a connection port of a supraglottic device (a laryngeal mask), or the like. The main port 12g is formed as a tube having a tapered shape. In the present embodiment, the outer diameter of the main port 12g having a tapered shape is increased such that the outer diameter on the distal end side is 21.5 mm and that the outer diameter on the proximal end side is 22.5 mm. The inner diameter of the main port 12g having a tapered shape is decreased such that the inner diameter on the distal end side is 15.5 mm and that the inner diameter on the proximal end side is 14.5 mm. Since the outer surface of the main port 12g forms a tapered shape, and the diameter of the tapered shape increases in a direction from the distal end side to the proximal end side of the main port 12g, variations of connection port diameters of tubes, which are connection targets, can be accommodated.

Note that the outer and inner diameters that have been mentioned above are examples.

The main port 12g is located at a position offset from the center of the bottom-surface portion 12b. If the main port 12g is formed at the center, the main port 12g will interfere with the above-mentioned bearing portion 12d. In order to avoid such an interference, a ventilation path extending from the ventilation path 16 to the main port 12g needs to be formed, and in order to form such a ventilation path, it is necessary to increase the size of the lid 12. In contrast, in the present embodiment, the main port 12g that communicates with the ventilation path 16 is located at the position offset from the center of the bottom-surface portion 12b, so that interference between the main port 12g and the bearing portion 12d is avoided. Thus, in the present embodiment, it is not necessary to increase the size of the lid 12, and the lid 12 and the ventilator 1 including the lid 12 can be compactly formed. In addition, since the main port 12g is located at the position offset from the center, the main port 12g and the valve body 9 are not in line with each other. In other words, the main port 12g and the valve hole 32b2 are formed at positions that are offset from each other. Thus, in the case where vomit or sputum flows backward from the main port 12g, the vomit or the sputum can be prevented from adhering to the valve body 9 and hindering an accurate operation.

Description of Pressure Setting Key 18

Figure 1:
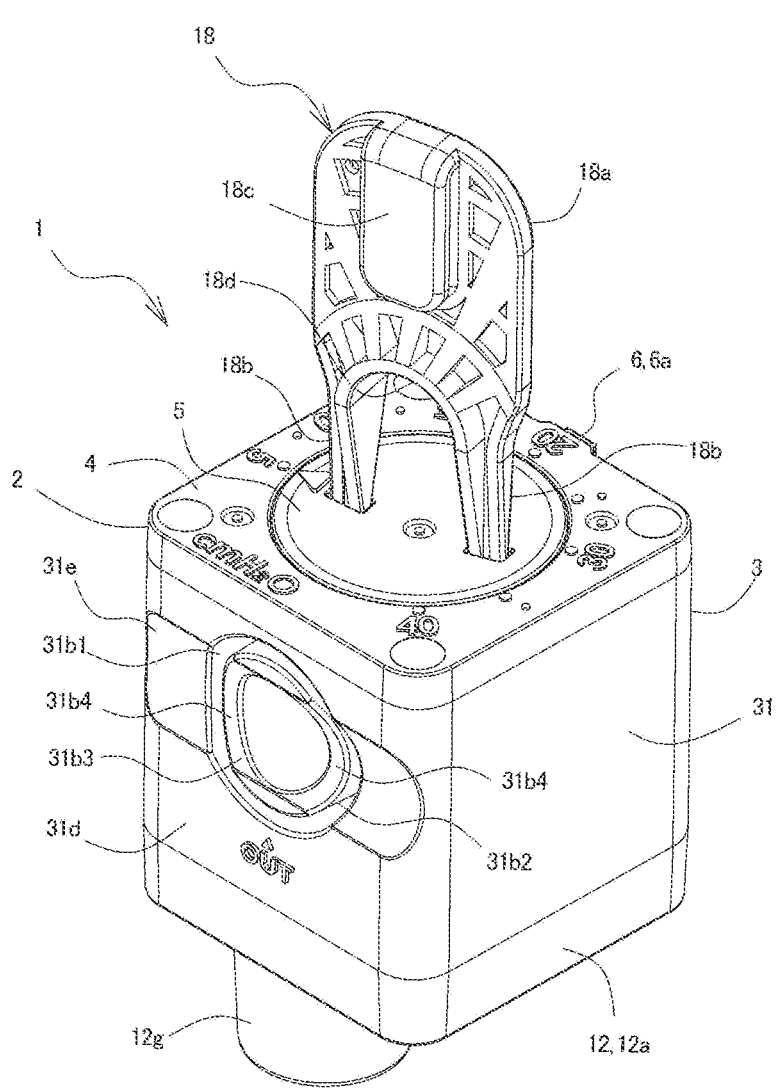
FIG. 1 is a perspective view including the front surface, the right-side surface, and a plan surface of a ventilator according to an embodiment.
Figure 2:
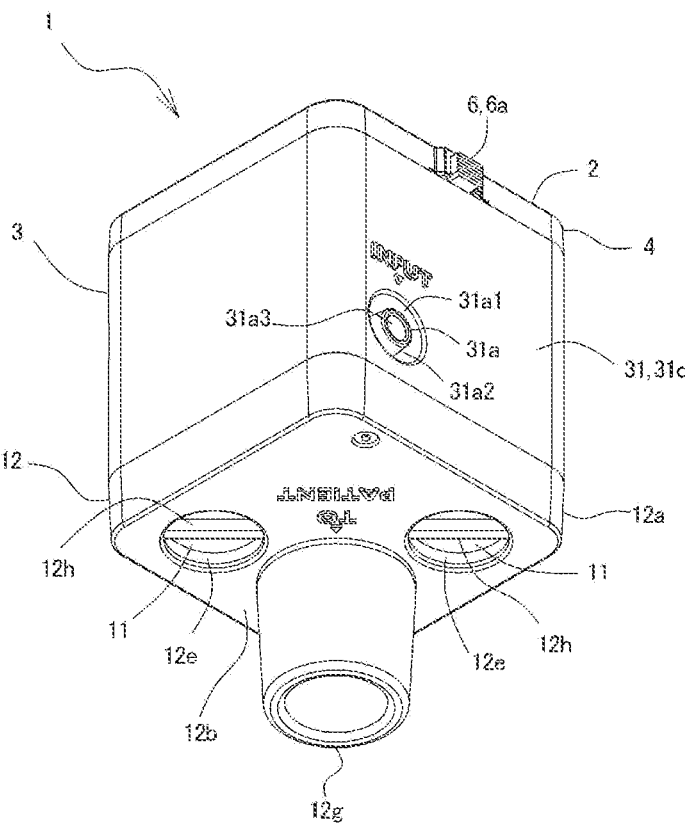
FIG. 2 is a perspective view including the rear surface, the right-side surface, and the bottom surface of the ventilator illustrated in FIG. 1.

As illustrated in FIG. 1, the pressure setting key 18 includes a key main body 18a and bifurcated key portions 18b extending from the key main body 18a. Note that FIG. 1 illustrates the pressure setting key 18 in a state where the key portions 18b are inserted in the key holes 50a.

A clip 18c is formed at the center of the key main body 18a and can be clipped on, for example, a chest pocket of a uniform worn by a healthcare worker. This can prevent a healthcare worker from losing the pressure setting key 18.

The ends of the key portions 18b can be inserted into the key holes 50a of the pressure setting dial 5. The pressure setting dial 5 can be rotated by holding and turning the key main body 18a in a state where the key portions 18b are inserted in the key holes 50a.

The key portions 18b can also be used as a disconnect wedge for disconnecting a connector such as a tracheal tube and a connector of a tube such as a catheter from each other. In the case of using the key portions 18b as a disconnect wedge, the key portions 18b can cause an arch portion 18d having an arc shape to be fitted on a tracheal tube.

Aspects of Medical Equipment Using Ventilator 1

The input port 31a of the ventilator 1 can be connected to a pipe for supplying air or a mixed gas of oxygen and air, an air or oxygen cylinder, an air compressor, or the like via an oxygen tube. The main port 12g can be connected to a connection port of a resuscitation mask that is worn on a patient, a connection port of a corrugated tube that is connected to a resuscitation mask, a nasal or oral endotracheal intubation tube, a tracheostomy tube, a connection port of a supraglottic device (a laryngeal mask), or the like. The exhaust port 31b can be connected to a corrugated tube, and for example, a purification filter for purifying an anesthetic gas contained in an exhausted gas (a gas exhaled by a patient) can be connected to the corrugated tube.

As described above, the ventilator 1 can be used for various purposes depending on the equipment that is combined with the ventilator 1, some uses of the ventilator 1 will be described below as examples. Configurations according to the following aspects may suitably include a corrugated tube or a breathing tube. In addition, in each of the following aspects, a configuration may be employed in which a tidal ventilation rate (a respiratory volume) can be monitored by providing, for example, a ventilation-volume measurement device such as a spirometer between a patient-side breathing member such as a resuscitation mask or an endotracheal intubation tube and the main port 12*g* of the ventilator 1.

[1] Manual Pulmonary Resuscitator

As the first aspect, the ventilator 1 includes at least the "patient-side breathing member" such as a resuscitation mask or an endotracheal intubation tube that is worn on a patient and connected to the main port 12*g* of the ventilator 1 and a "manual gas supply device" such as a resuscitation bag or a foot pump that is connected to the input port 31*a* of the ventilator 1, so that the ventilator 1 can be implemented as a "manual pulmonary resuscitator". According the present aspect, a general manual pulmonary resuscitator can have a function of serving as a ventilator. Regarding a method of supplying air, which is used as power, the air can be supplied without expert knowledge. The relief valve 14 can automatically adjust the pressure, and thus, the ventilator 1 can be used safely also by hand as long as the air is continuously supplied by squeezing the resuscitation bag or stepping on the foot pump. In addition, it will be convenient if a foot pump is used because ventilation can be performed by using a foot, and both hands are free, so that a patient can be treated at the same time. This manual pulmonary resuscitator can further include a gas supply source that supplies oxygen gas or a mixed gas and that is connected to the manual gas supply device such as a resuscitation bag.

[2] Ventilator Unit

As the second aspect, the ventilator 1 includes at least the "patient-side breathing member", such as a mask or an intubation tube, that is worn on a patient and connected to the main port 12*g* of the ventilator 1 and a "gas supply source" that is connected to the input port 31*a* of the ventilator 1 and that supplies, for example, a mixed gas of oxygen and air as a "gas", so that the ventilator 1 can be implemented as a pneumatically-operated "ventilator unit". According to the present aspect, even in a situation in which a ventilator equipped with an electrical driving source cannot be used, examples of the situation including during an earthquake, in case of power outage, and when all ventilators are in use and there is no available ventilator, artificial respiration can be performed.

[3] Inhalation Anesthesia Apparatus

As the third aspect, the ventilator 1 includes at least the "patient-side breathing member", such as a mask, that is worn on a patient and connected to the main port 12*g* of the ventilator 1, an "anesthetic-gas supply source" that is connected to the input port 31*a* of the ventilator 1 and that supplies an anesthetic gas as a "gas", and an "anesthetic-gas purification filter" that is connected to a corrugated tube connected to the exhaust port 31*b*, so that the ventilator 1 can be implemented as an "inhalation anesthesia apparatus". According to the present aspect, the inhalation anesthesia apparatus can be fabricated with a simple machine structure.

Advantageous Effects of Ventilator 1

Advantageous effects of main configurations in the embodiment will now be described.

The ventilator 1 includes the housing 2, the housing 2 has the input port 31*a* through which a gas is introduced into the housing 2, the main port 12*g* through which the gas that is to be sent to and inhaled by a patient and a gas exhaled by the patient pass, the exhaust port 31*b* through which the gas inhaled or the exhaled gas is exhausted from the housing 2, the ventilation path 16 connecting the input port 31*a* and the main port 12*g* to each other, and the relief valve 14 that is opened by receiving the pressure from the ventilation path 16 and that allows communication between the ventilation path 16 and the exhaust port 31*b* so as to release the pressure. The ventilator 1 integrally includes these components as described above, and thus, the ventilator 1 does not require an electrical driving source, and a new device for a pulmonary resuscitator that functions as a mechanical ventilator with a simple structure can be provided.

The ventilator 1 can be configured as a single-use "disposable ventilator". This configuration can help to prevent infectious diseases from occurring due to usage the same ventilator 1 for a plurality of patients. In addition, in this case, if all the components of the ventilator 1 are formed of resin-molded bodies, the ventilator 1 can be configured as a "disposable ventilator" that does not need to be separated into a metal member and a resin member for disposal.

The housing 2 further includes the HME filter 10 disposed between the main port 12*g* and the exhaust port 31*b*. According to this configuration, since the ventilator 1 includes the HME filter 10 built therein, a healthcare worker does not need to prepare a device for an HME filter in addition to the ventilator 1.

Figure 3:
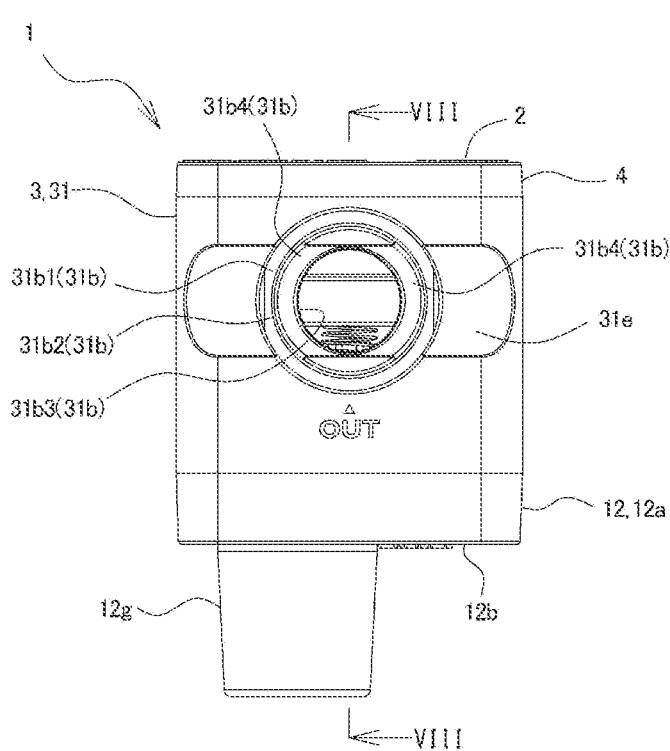
FIG. 3 is a front view of the ventilator illustrated in FIG. 1.
Figure 4:
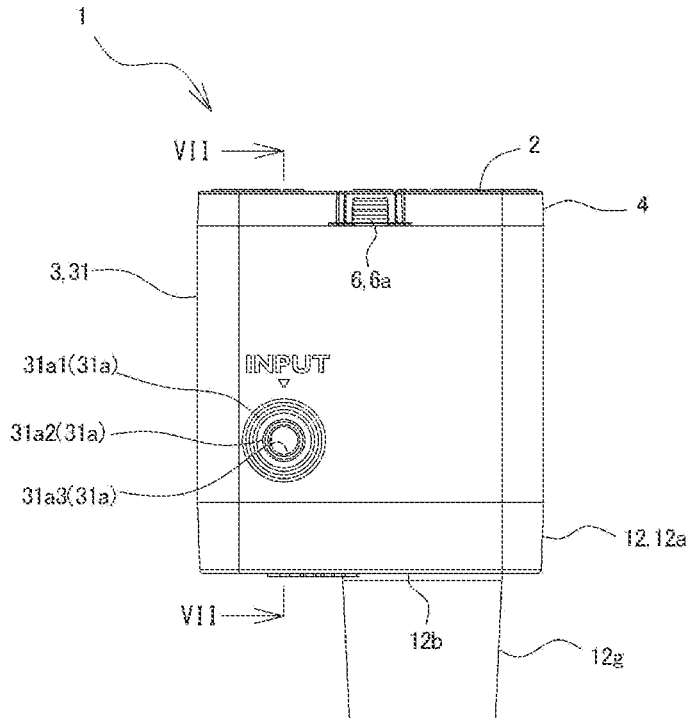
FIG. 4 is a rear view of the ventilator illustrated in FIG. 1.

The housing 2 has the input port 31*a*, the exhaust port 31*b*, the ventilation path 16, and the relief valve 14 built therein. Thus, the number of geometrical elements protruding outside the housing 2 can be reduced, and the ventilator 1 can be compactly formed. As an example, the ventilator 1 of the present embodiment can be implemented such that, for example, its height including the main port 12*g* (the length from the upper surface of the dial cover 4 to the lower end of the main port 12*g* in the front view illustrated in FIG. 3), its width (the length of the ventilator 1 in the horizontal direction in FIG. 5), and its depth (the length of the ventilator 1 excluding the unlock button 6 in the vertical direction in FIG. 5) are 77.2 mm, 50.0 mm, 50.0 mm, respectively.

The housing 2 further has the spontaneous-breathing openings 12*e* formed therein and includes the valve films 11 functioning as the spontaneous-breathing valves that are opened by the inspiratory pressure, at which a patient spontaneously breathes, so as to allow communication between the ventilation path 16 and the outside of the housing 2. According to this configuration, even if a patient who is unconscious and is under mechanical ventilation using the ventilator 1 suddenly awakes and spontaneously take a deep breath, the valve films 11 are opened and can help the patient breathe.

Modifications of Embodiment

In the above-described embodiment, although the valve shaft 9*d* is formed of a metal bar and integrated with the base 9*a* of the valve body 9 as an example, the method of fabricating this integral structure is not limited to insert molding, and a different integral structure that is fabricated by bonding using an adhesive, fixation using a screw, or the like can also be employed. According to this configuration, the structure in which the valve body 9 and the valve shaft 9*d* are integrated with each other can be easily fabricated.

In the above-described embodiment, although the valve shaft 9*d* is formed of a metal bar as an example, the valve shaft 9*d* can be formed as a portion of the base 9*a* of the valve body 9. According to this configuration, the entire valve body 9 is formed of a resin-molded body, and the number of components can be reduced, so that cost reduction can be achieved. In this case, if a composite spring is used as the pressure setting spring 8, and plastic screws are used as the screws 13 instead of using metal screws, all the components of the ventilator 1 can be formed of resin-molded bodies, and an MRI room where metal objects cannot be taken into can be used while the ventilator 1 is worn. In addition, a reduction in the manufacturing costs can also be achieved.

In the above-described embodiment, although each of the components of the ventilator 1 is formed of a resin-molded body as an example, each resin-molded body may be a body formed by 3D printing rather than a body molded by using a metal mold. According to this configuration, each component of the ventilator 1 can be manufactured by using a 3D printer, and it is not necessary to prepare an expensive metal mold. In addition, the ventilator 1 can be manufactured and used in, for example, in a remote area or an isolated island with underdeveloped distribution of goods and inconvenient transportation or even in a space station. Furthermore, it is economical because only a required number of the ventilators 1 can be manufactured.

In the above-described embodiment, although each of the components of the ventilator 1 is made of a resin as an example, some or all of the components may be made of a metal. In the case where some or all of the components are made of a metal, these components may each be any body such as a cutting body, a casting body, a 3D printed body that is formed by using a metal 3D printer, regardless of a difference in a basic manufacturing method, as long as they are made of a metal material. As a result, the durability of the ventilator 1 and the durability of each component can be improved.

In the above-described embodiment, although the input port 31*a* and the exhaust port 31*b* do not project from the outer surface of the housing 2 as an example, the input port 31*a* and the exhaust port 31*b* may each have a shape protruding from the housing 2 like the main port 12*g*. According to this configuration, it can be determined by visual observation whether a pipe is properly connected to the input port 31*a* or the exhaust port 31*b*. In the above-described embodiment, although the main port 12*g* protrudes from the outer surface of the housing 2 as an example, the main port 12*g* can be formed so as not to protrude from the housing 2 like the input port 31*a*. According to this configuration, since the main port 12*g* does not protrude, the ventilator 1 can be compactly formed and can be prevented from breaking.

In the above-described embodiment, although the ventilation grooves 31*e* are each formed in the second outer surface 31*d* of the main body 3 in such a manner as to extend from the exhaust port 31*b* as an example. However, an exhaust path extending from the outlet 31*b*3 can be formed also by, for example, forming a projection on the second outer surface 31*d* or providing a porous member (e.g., a piece of mesh, a piece of breathable sponge, or the like) on the second outer surface 31*d*.

In the above-described embodiment, although the ventilation path 16 is formed of the first ventilation spaces 34 of the main body 3 and the second ventilation space 12*c* of the lid 12 as an example, a "ventilation path" may be formed one of the main body 3 or the lid 12.

In the above-described embodiment, although a rotary operation of the pressure setting dial 5 is performed by using the pressure setting key 18, which is a dedicated device for pressure setting, as an example, the pressure setting dial 5 may be provided with an operation knob, and the rotary operation may be performed by using the operation knob. According to this configuration, the rotary operation can be easily performed.

In the above-described embodiment, although the click generating unit 15 that generates a clicking sensation upon rotation of the pressure setting dial 5 is provided as an example, a latching mechanism that stops rotation of the pressure setting dial 5 for each predetermined rotation amount, by which a set pressure value changes, and locks the pressure setting dial 5 may be provided. Such a latching mechanism can be formed so as to have a configuration in which, for example, a locking member such as the unlock button 6 engages with, by being pressed and urged by a spring or the like, a portion of the outer peripheral surface of the pressure setting dial 5, the portion having irregularities formed of an inclined surface and a step surface that are continuous with each other. According to this configuration, the pressure setting dial 5 is locked each time the pressure setting dial 5 is rotated, and thus, a set pressure value can be prevented from being unexpectedly changed as a result of the pressure setting dial 5 coming into contact with something.

In the above-described embodiment, although the dial cover 4 includes the display portions 4*a*, which are formed as portions of a resin-molded body and which display letters and numbers, and the set-pressure-value indication portion 50*e*, which is formed of a resin-molded body so as to have the shape of a symbol, as an example, and similarly, sets of English letters "INPUT", "OUT", and "PATIENT" and triangular symbols are formed on the housing 2 as an example. However, they can be formed of laser engraved portions or can be formed of printed stickers placed on the dial cover 4 and the housing 2.

Note that, although the embodiment has been described in detail above as an aspect of the present disclosure, those skilled in the art will easily understand that many modifications may be made without substantially departing from the configurations and the effects of the present invention. Therefore, all such modifications are included in the scope of the present invention.

For example, a term that is mentioned in the specification or the drawings at least once together with a different term that has a wider meaning or a similar meaning can be replaced with the different term anywhere in the specification or the drawings. In addition, the configurations and the operations of the ventilator 1, the ventilator unit, the manual pulmonary resuscitator, the inhalation anesthesia apparatus are not limited to those described as an embodiment of the present invention, and various modifications can be made.

REFERENCE SIGNS LIST

1 ventilator
2 housing
3 main body
30 upper surface wall
30*a* insertion hole
30*b* engagement recess
31 outer peripheral wall
31*a* input port
31*a*1 input-port recess
31*a*2 first connection pipe
31*a*3 introduction port
31*b* exhaust port
31*b*1 exhaust-port recess
31*b*2 second connection pipe
31*b*3 outlet
31*b*4 curved recess
31*c* first outer surface
31*d* second outer surface
31*e* ventilation groove
32 accommodating unit
32*a* cylindrical portion 32*a*1 guide
32*b* bottom-surface portion
32*b*1 valve seat
32*b*2 valve hole
32*c* accommodating space
32*c*1 valve chamber
33 support wall
33*a* first support wall
33*a*1 first leg portion
33*a*2 first holding portion
33*b* second support wall
33*b*1 second leg portion
33*b*2 second holding portion
33*c* third support wall
34 first ventilation space
34*a* input-side ventilation space
4 dial cover
4*a* display portion
4*b* arrangement recess
4*b*1 guide recess
4*c* arrangement opening
4*d* rotation guide
4*d*1 first contact receiving portion
4*d*2 second contact receiving portion
4*d*3 third contact receiving portion
5 pressure setting dial
50 dial main body
50*a* key hole
50*b* protruding cylinder
50*c* external thread
50*d* spring accommodating portion
50*e* set-pressure-value indication portion
51 flange
52 stopper
52*a* thick portion
52*b* thin portion
53 engagement piece
53*a* small projection
6 unlock button (unlocking unit)
6*a* pushing-operation portion
6*b* push portion
6*b*1 guide projection
6*b*2 inclined-surface portion
7 holder
7*a* holder main body
7*b* cylindrical protruding portion
7*c* guide projection
7*d* internal thread
8 pressure setting spring
9 valve body
9*a* base
9*a*1 first pressure-receiving surface portion
9*a*2 cylindrical protrusion
9*b* annular portion
9*b*1 second pressure-receiving surface portion
9*c* cylindrical surrounding wall
9*c*1 spherical outer peripheral surface
9*d* valve shaft
10 heat and moisture exchanger (HME) filter
10*a* insertion hole
10*b* groove
10*c* positioning portion
11 valve film (spontaneous-breathing valve)
12 lid
12*a* outer peripheral wall
12*a*1 screw hole
12*b* bottom-surface portion 12*c* second ventilation space
12*d* bearing portion (shaft hole)
12*e* spontaneous-breathing opening (spontaneous-breath-ing valve)
12*f* arrangement recess
12*g* main port
12*h* support portion
13 screw
13*a* sealing portion
14 relief valve
15 click generating unit
16 ventilation path
17 rotation unlock mechanism
18 pressure setting key
18*a* key main body
18*b* key portion
18*c* clip
18*d* arch portion

The invention claimed is:

1. A ventilator comprising:
a housing,
wherein the housing has
an outer peripheral wall,
a lid, the lid and the outer peripheral wall cooperatively defining the housing,
an input port, formed on the outer peripheral wall, through which a gas is introduced into the housing,
a main port, formed on a bottom surface of the housing, through which the gas that is to be sent to and inhaled by a patient and a gas that is exhaled by the patient pass,
an exhaust port, formed on the outer peripheral wall, through which the gas to be inhaled or the gas exhaled is exhausted from the housing,
a heat and moisture exchanger filter disposed inside the housing and between the main port and the exhaust port,
a ventilation path connecting the input port and the main port to each other, and
a relief valve, formed inside the housing, that includes a valve body configured to be opened by receiving a pressure from the ventilation path and that allows communication between the ventilation path and the exhaust port in such a manner as to release the pressure.

2. The ventilator according to claim 1,
wherein the input port, the exhaust port, the ventilation path, and the relief valve are arranged inside the housing.

3. The ventilator according to claim 1,
wherein the housing further includes a spontaneous-breathing valve that is opened by an inspiratory pressure at which the patient spontaneously breathes in such a manner as to allow communication between the ventilation path and an area outside the housing.

4. The ventilator according to claim 3,
wherein the spontaneous-breathing valve has a spontane-ous-breathing opening formed in the housing and a valve film closing the spontaneous-breathing opening, the valve film being configured to be opened toward the inside of the housing by an inspiratory pressure at which a patient spontaneously breathes.

5. The ventilator according to claim 1,
wherein the housing has a shape of a box-shaped poly-hedron.

6. The ventilator according to claim 1,
wherein the housing is a resin-molded body.

7. The ventilator according to claim 1,
wherein the input port is disposed inside the housing and includes a first connection pipe having an introduction port that is open toward an outside of the housing.

8. The ventilator according to claim 1,
wherein the exhaust port is disposed inside the housing and includes a second connection pipe having an outlet that is open toward an outside of the housing.

9. The ventilator according to claim 8,
wherein the outlet has a curved recess that is recessed toward the inside of the housing from the outer peripheral wall.

10. The ventilator according to claim 8,
wherein a ventilation groove is formed in an outer surface of the housing, the outer surface having the exhaust port, in such a manner as to communicate with the outlet and to extend to an outer edge of the outer surface.

11. The ventilator according to claim 1,
wherein the relief valve further includes
a pressure setting dial that has a disc-like shape and that is configured to be rotated to enable setting of the pressure at which the valve body is opened and
a dial cover holding the pressure setting dial such that the pressure setting dial is rotatable.

12. The ventilator according to claim 1,
wherein the relief valve further includes a valve shaft that is integrally formed with the valve body and that supports movement of the valve body, and
wherein the housing includes a bearing portion that guides movement of the valve shaft.

13. The ventilator according to claim 1, wherein the input port has a shape protruding from the housing.

14. The ventilator according to claim 13, wherein the main port is formed as a cylindrical pipe protruding outward from a bottom surface of the lid.

15. The ventilator according to claim 1, wherein the exhaust port has a shape protruding from the housing.

16. The ventilator according to claim 1, wherein
the lid has an outer peripheral wall and a bottom-surface portion, and
the heat and moisture exchanger filter is disposed in a space formed and defined by the outer peripheral wall and the bottom-surface portion.

17. The ventilator according to claim 1, wherein the input port is recessed towards the inside of the housing from the outer peripheral wall.

18. A ventilator unit comprising:
the ventilator according to claim 1; and
a patient-side breathing member one end of which is connected to the main port of the ventilator and another end of which is connected to a patient.

19. A manual pulmonary resuscitator comprising:
the ventilator according to claim 1.

20. An inhalation anesthesia apparatus comprising:
the ventilator according to claim 1.

21. A ventilator comprising:
a housing,
wherein the housing has
an input port through which a gas is introduced into the housing,
a main port through which the gas that is to be sent to and inhaled by a patient and a gas that is exhaled by the patient pass,
an exhaust port through which the gas inhaled or the gas exhaled is exhausted from the housing,
a ventilation path connecting the input port and the main port to each other, and
a relief valve that includes a valve body configured to be opened by receiving a pressure from the ventilation path and that allows communication between the ventilation path and the exhaust port in such a manner as to release the pressure,
wherein the relief valve further includes
a pressure setting dial that has a disc-like shape and that is configured to be rotated to enable setting of the pressure at which the valve body is opened, and
a dial cover holding the pressure setting dial such that the pressure setting dial is rotatable,
wherein the dial cover includes a contact receiving portion that stops rotation of the pressure setting dial by coming into contact with the pressure setting dial, and
wherein the pressure setting dial includes a stopper that comes into contact with the contact receiving portion at a position at which an intermediate set pressure between a minimum set pressure and a maximum set pressure is set.

22. The ventilator according to claim 21,
wherein the relief valve further includes an unlock button that releases contact between the stopper and the contact receiving portion by pushing the stopper and releases a rotation stop of the pressure setting dial heading in a direction from the intermediate set pressure toward the maximum set pressure.

\* \* \* \* \*